US008313327B1

(12) United States Patent
Won

(10) Patent No.: US 8,313,327 B1
(45) Date of Patent: Nov. 20, 2012

(54) ORTHODONTIC DEVICES

(76) Inventor: Joon Won, San Jose, CA (US)

( * ) Notice: Subject to any disclaimer, the term of this patent is extended or adjusted under 35 U.S.C. 154(b) by 0 days.

(21) Appl. No.: 13/294,190

(22) Filed: Nov. 11, 2011

(51) Int. Cl.
*A61C 3/00* (2006.01)
(52) U.S. Cl. .............................................. 433/7; 433/23
(58) Field of Classification Search .................. 433/6–7, 433/18, 23
See application file for complete search history.

(56) References Cited

U.S. PATENT DOCUMENTS 1,369,665 A * 2/1921 Johnson ........................... 433/14
6,267,589 B1 * 7/2001 Farzin-Nia et al. ................ 433/7

* cited by examiner

*Primary Examiner* — Heidi M Eide
(74) *Attorney, Agent, or Firm* — Patent Office of Dr. Chung Park

(57) ABSTRACT

Devices for applying orthodontic forces. A device includes an adaptor having a housing section configured to fit directly onto a sheath of a molar band and a tube section having an elongated bore. The device also includes a pin having a head portion and a tail portion, where the tail portion is slidably mounted into the elongated bore of the tube section. The head portion of the pin is adapted to slide into the sheath to thereby detachably lock the adaptor to the molar band.

6 Claims, 4 Drawing Sheets

ORTHODONTIC DEVICES

FIELD OF INVENTION

The present invention relates to orthodontic devices, and more particularly, to detachable devices for performing dental procedures.

BACKGROUND OF INVENTION

A fundamental objective in orthodontics is to realign a patient's teeth to positions where the teeth function optimally and aesthetically. In general, various types of appliances, such as bite plate and expansion device, are applied to the teeth of the patient. In conventional approaches, each device is welded to two or more molar bands that are secured on molar teeth. Such conventional approaches have several disadvantages. First, the molar bands for securing one appliance should be removed when the dentist wants to mount a new appliance since each appliance is welded to at least two molar bands. Removing and installing molar bands require considerable skills and effort of the dentist. Also, the used molar bands are discarded with the appliance since the molar bands and the appliance are designed to fit to only a specific patient and typically prepared by an experienced dental technician before the patient visits the dentist. Thus, the conventional appliance designs produce waste in terms of material and efforts.

Second, the dentist has limited flexibility in treating the patients, i.e., the dentists cannot change the treatment procedure easily once an appliance is mounted to the patient's teeth. Furthermore, the dentist cannot easily change the type of appliance or modify the appliance in his office, and, as a consequence, the treatment procedure may be extended if the pre-fabricated appliance has a defect or does not perfectly fit to the patient's dental configuration. As such, there is a strong need for orthodontic devices that can be mounted/dismounted without removing the molar bands from the molar teeth of the patient.

SUMMARY OF INVENTION

In one aspect of the invention, a device for mounting an orthodontic appliance includes: an adaptor having a housing section configured to fit directly onto a sheath of a molar band and a tube section having an elongated bore for receiving a portion of the orthodontic appliance; and a pin having a head portion and a tail portion, the tail portion being slidably mounted into the elongated bore of the tube section. The head portion of the pin is adapted to slide into the sheath to thereby detachably lock the adaptor to the molar band.

In another aspect of the invention, a device for applying orthodontic forces includes: an adaptor having a housing section configured to fit directly onto a sheath of a molar band and a tail section having an elongated bore; and a pin having a head portion and a tail portion, the tail portion being slidably mounted into the elongated bore of the tube section. The head portion of the pin is adapted to slide into the sheath to thereby detachably lock the adaptor to the molar band.

BRIEF DESCRIPTION OF DRAWINGS

These and other features of the invention will now be described with reference to the drawings summarized below. These drawings and the associated description are provided to illustrate preferred embodiments of the invention and are not intended to limit the scope of the invention.

DETAILED DESCRIPTION OF EXEMPLARY EMBODIMENTS

Although this invention will be described in terms of certain preferred embodiments, other embodiments that are apparent to those of ordinary skill in the art, including embodiments that do not provide all of the benefits and features set forth herein, are also within the scope of this invention. Accordingly, the scope of the invention is defined only by reference to the appended claims.

Figure 1:
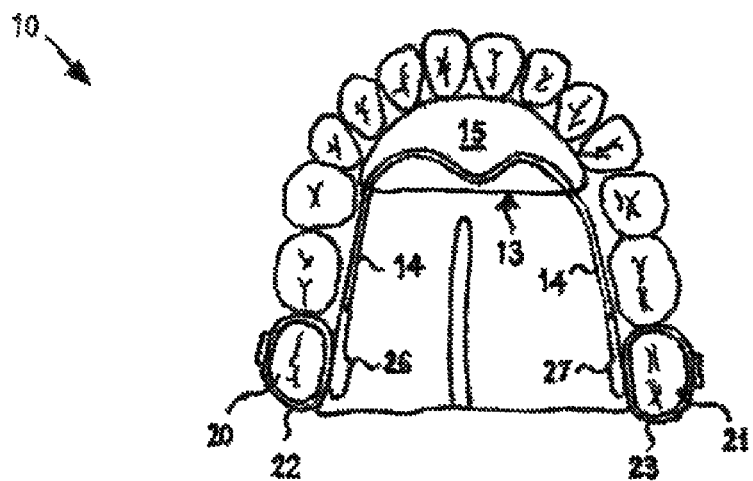
FIG. 1 is a schematic diagram of an upper dental arch having a bite plate detachably mounted to a pair of molar bands.

Now referring to FIG. 1, FIG. 1 is a schematic diagram of an upper dental arch 10 having a bite plate 13 detachably mounted to a pair of molar bands 22 and 23 in accordance with one embodiment of the present invention. As depicted, bite plate 13 includes a body 15 and a pair of legs 14, and is fitted to the palate as a diagnostic or therapeutic aid in orthodontics or prosthodontics. The body 15 may be formed of plastic or silicon or both. The pair of legs 14 may be made of a piece of wire, where the middle portion of the wire is embedded in the body 15.

A pair of molar bands 22 and 23 may be installed around a pair of second molars 20 and 21 (or any other posterior teeth), where the molar bands 22 and 23 may be of conventional type, such as molar band sold under the trademark ROLLO™ BAND, manufactured by American Orthodontics at Sheboygan, Wis. As described in conjunctions with FIGS. 2A-2B, the tip portions of the legs 14 of the bite plate 13 slidably engage into the tube sections of the adaptors 26 and 27 so that the entire bite plate 13 is detachably mounted to the molar bands 22 and 23, respectively.

Figure 2B:
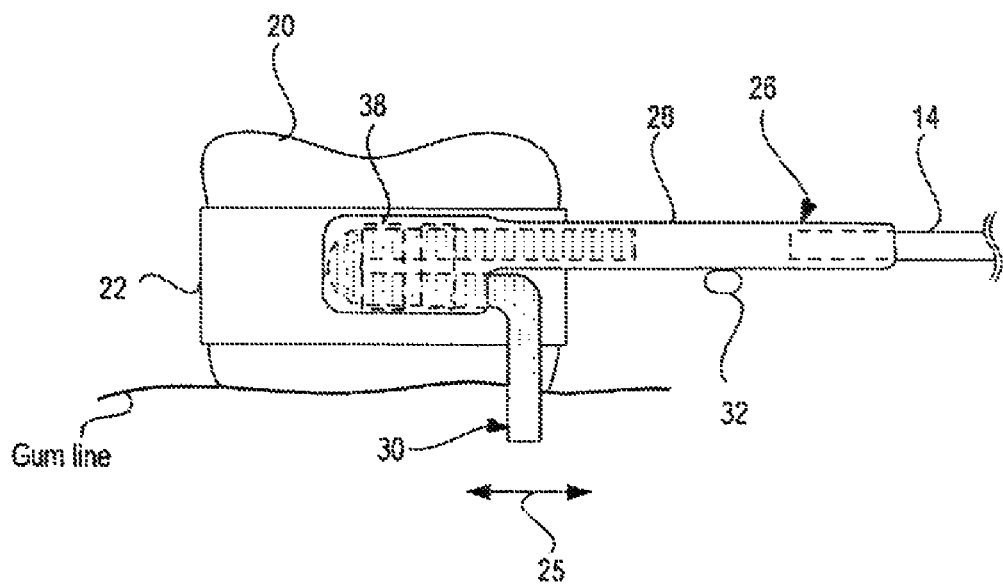
FIG. 2B is a side view of the adaptor in FIG. 1.
Figure 2A:
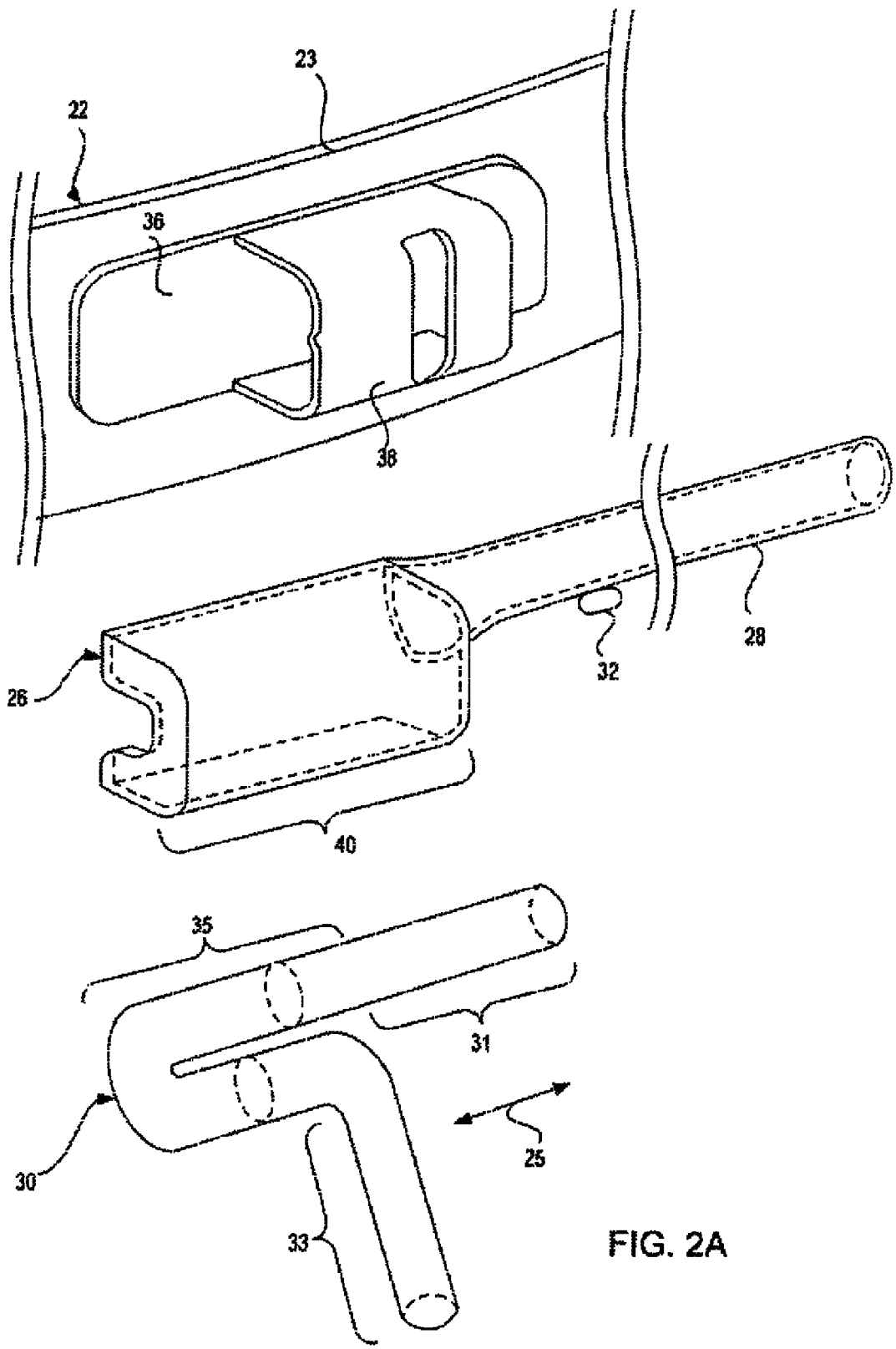
FIG. 2A is an exploded view of the adaptor in FIG. 1.

FIG. 2A is an exploded view of the adaptor 26 in FIG. 1, where the adaptor 26 is mounted directly to the molar band 22. As depicted, the molar band 22 includes: a ring or circular strip 23 tightly fitted to the molar 20; a base plate 36 secured (such as welded) to the ring 23; and a sheath 38 secured to the base plate 36. The sheath 38 forms a channel for receiving the head (or, head portion) 35 of the pin 30. The adaptor 26 includes a housing section 40, a tube section 28 having an elongate bore therein, and optionally a bump 32. The housing section 40, which is preferably formed of metal, is dimensioned to fit directly onto the outer surface of the sheath 38. For example, the sheath 38 snaps into the housing section 40 so that the sheath 38 remains in firm contact with the housing section 40 upon mounting the adaptor 26 to the sheath 38.

The inner diameter of the tube section 28 is slightly larger than the diameter of the tail (or, tail portion) 31 of the pin 30 so that the tail 31 can be inserted in and slide relative to the tube section 28. (As will be discussed in conjunction with FIGS. 3A-3B, the dentist may hold the handle 33 of the pin 30 to move the pin 30 relative to the tube section along the direction 25, to thereby lock/release the adaptor 26 to/from the molar band 22.) The cross sectional shape of the tail 31, which is preferably a circle, is the same as that of the tube section 28.

The head 35 of the pin 30 has a generally U-shape and dimensioned to fit into the sheath 38 when the dentist locks the adaptor 26 to the molar band 22. Preferably, the entire portion of the pin 30 may be formed by bending one piece of circular wire (or thin rod). Optionally, the adaptor 26 has a bump 32 disposed on the outer surface of the tube section 28, where the dentist may grip both the bump 32 and the handle 33 simultaneously with his pliers when he releases the adaptor 26 from the molar band 22. Both the adaptor 26 and the pin 30 may be formed of suitable materials, such as metals.

FIG. 2B is a side view of the adaptor 26 mounted and locked to the molar band 22, where the molar band 22 is mounted on the molar 20. For the purpose of illustration, the sheath 38 of the molar band 22 is also shown therein. As depicted, the head 35 of the pin 30 is inserted into the sheath 38 while a portion of the tail 31 of the pin 30 is inside the tube section 28 of the adaptor 26. Thus, in the locking position, the pin 30 is holding the sheath 38 and the adaptor 26 together. A tip portion of the leg 14 of the bite plate 13 is inserted into the tube section 28 so that the bite plate 13 is mounted to the adaptor 26.

When the dentist wants to dismount the bite plate 13 from the molar band 22, he may release the adaptor 26 from the molar band 22 by pulling the handle 33 of the pin 30 toward the bump 32 and, subsequently, taking the housing section 40 off of the adaptor 26. Also, the dentist may disengage the leg 14 from the tube section 28 of the adaptor 26. As such, the adaptor 26 allows the dentist to detachably mount the bite plate 13 to the molar band 22, i.e., the dentist can mount/dismount the bite plate 13 without taking the molar band 26 off of the molar 20. The adaptor 27 is similar to the adaptor 26, with the difference that they have symmetric to each other. As such, the detailed description of the adaptor 27 is not repeated for brevity.

Figure 3A:
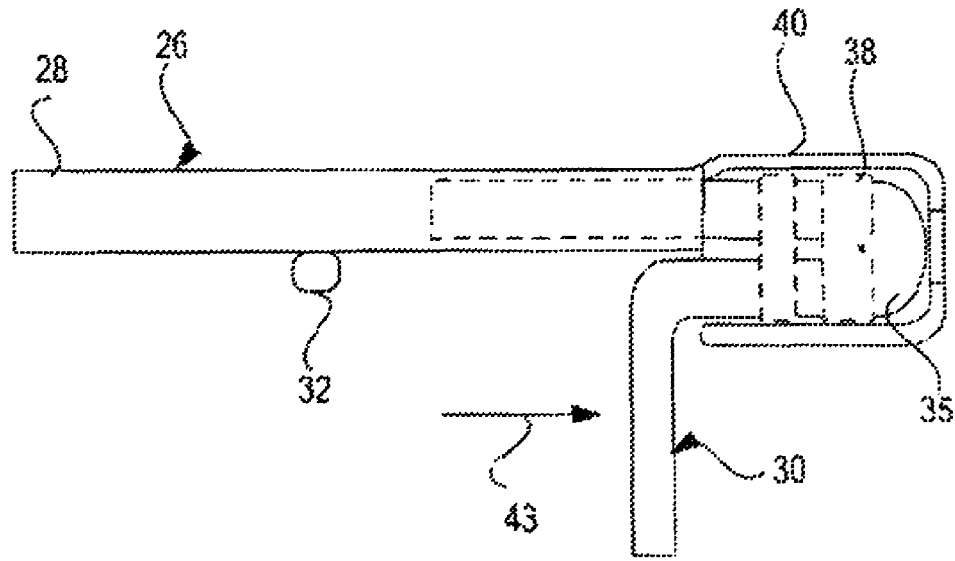
FIG. 3A is a schematic diagram of the adaptor in FIG. 1, where the adaptor is in the locking position.
Figure 3B:
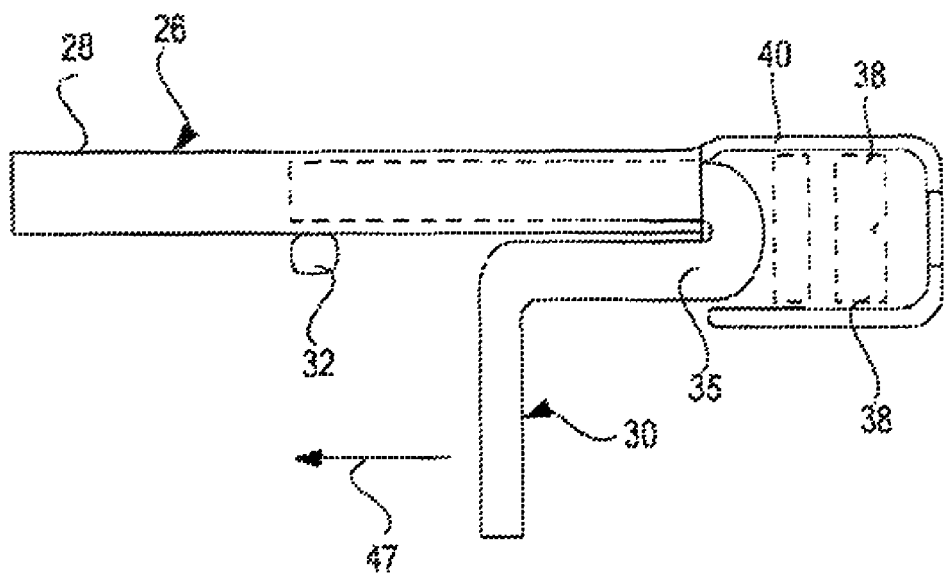
FIG. 3B is a schematic diagram of the adaptor in FIG. 1, where the adaptor is in the release position.

FIG. 3A is a schematics diagram of the adaptor 26 in FIG. 1, where the adaptor 26 is in the locking position. FIG. 3B is a schematics diagram of the adaptor 26 in FIG. 1, where the adaptor 26 is in the release position. For the purpose of illustration, the sheath 38 is also indicated in FIGS. 3A-3B. As depicted, the dentist may push the handle 33 of the pin 30 along the direction 43 so that the head 35 of the pin 30 fully engages into the sheath 38 and thus, the pin 30 holds both the sheath 38 and the adaptor 26. To release the adaptor 26 from the sheath 38, the dentist may push the handle 35 along the direction 47. Once the head 35 of the pin 30 is fully disengaged from the sheath 38, the dentist may take the housing section 40 of the adaptor 26 off of the sheath 38.

Figure 4:
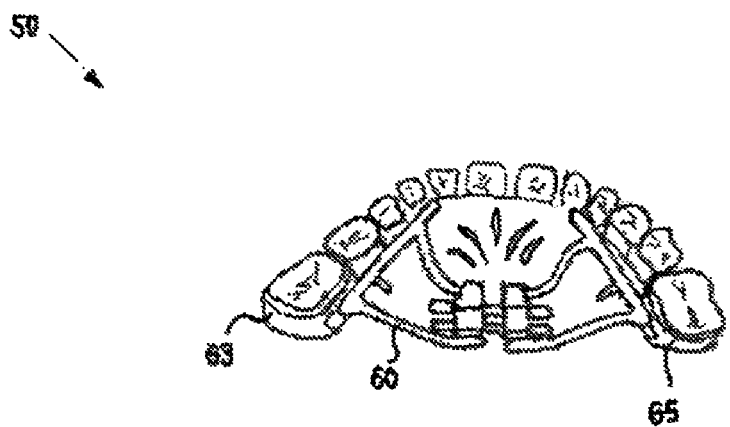
FIG. 4 is a schematic diagram of an upper dental arch having an extension device detachably mounted to a pair of molar bands.
Figure 5:
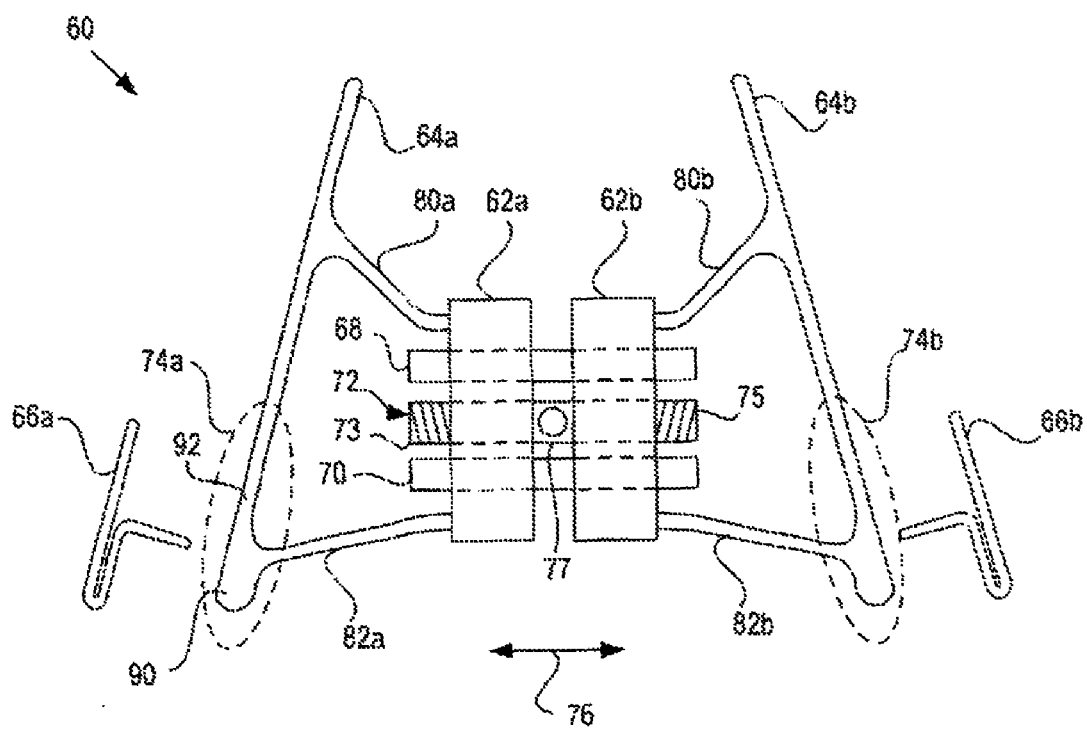
FIG. 5 is a schematic diagram of the expansion device in FIG. 4.

FIG. 4 is a schematic diagram of an upper dental arch 50 having an extension device 60 detachably mounted to a pair of molar bands 63 and 65. FIG. 5 is a schematic diagram of the expansion device 60 in FIG. 4. As depicted, the expansion device 60 includes: two support rods 64a, 64b; a left body 62a; a right body 62b; and arms 80a, 80b, 82a, and 82b connected to the support rods 64a and 64b, left body 62a, and right body 62b; and a screw member 72 operatively connected between the left body 62a and the right body 62b. The screw member 72 is adjustable to cause the left body 62a and the right boy 62b to move away from one another. It can also cause them to move toward one another while developing an orthopedic force between them.

The expansion device 60 further includes two slide rods 68 and 70, one on each side of the screw member 72. The screw member 72 has a first section 73 having screw threads formed in one direction and a second section 75 having screw threads formed in the opposite direction. An adjuster block 77 is located between the two sections 73 and 75 of the screw member 72.

The left body 62a has a hole having screw threads cut into it to receive the first section 73. The right body 62b has a hole having screw threads cut into it to receive the second section 75. The sections 73 and 75 of the screw member 72 are attached to opposite sides of an adjuster block 77. The adjuster block 77 has a hole in it. The hole allows an adjustment key to be placed in it by a dentist or a patient to adjust a level of force to be applied between the molar bands 63 and 65. The screw sections 73 and 75 are threaded in opposite directions so that as they turn with the rotation of the adjuster block 77, the left body 62a and right body 62b are drawn toward one another or away from on another depending on the direction in which the screw member 72 is turned.

The expansion device 60 includes a pair of adaptors 74a and 74b that are respectively similar to the adaptors 26 and 27 in FIGS. 1-3B. More specifically, the adaptor 74a (and 74b) includes a housing section 90 and tube section 92 that have similar structures as the housing section 40 and the tube section 28 of the adaptor 26, respectively. The expansion device 60 further includes a pair of pins 66a and 66b that are used to lock adaptors 74a and 74b to the sheaths of the molar bands 63 and 65, respectively. Since the structure and operational mechanism of the adaptors 74a and 74b are similar to the adaptors 26 and 27 in FIGS. 1-3B, the detailed description of the adaptors 74a and 74b are not repeated for brevity.

Since the molar bands 22 and 23 are identical to the molar bands 63 and 65, respectively, the expansion device 60 may be mounted to the same molar bands after the dentist dismounts the bite plate 13 from the molar bands. As such, the same molar bands can be used in performing two different treatments. In fact, the molar bands 63 and 65 (or, equivalently 22 and 23) may be used to detachably mount any other type of orthodontic appliance that has adaptors similar to the adaptors 26 and 27 in FIG. 1, while the dentist does not need to remove the molar bands 63 and 65 from the molar teeth. Compared to the conventional orthodontic appliances, the present feature provides various advantages; (1) unlike the conventional appliances, the molar bands 63 and 65 are not welded to the expansion device 60 and, as such, the molar bands 22 and 23 used to mount the bite plate 13 can be reused to mount the expansion device 60. The dentist can save time and effort to remove the molar bands each time he mounts a conventional appliance to the patient's teeth, obviating the waste of molar bands. (2) The dentist can easily and quickly dismount an orthodontic appliance from the molar bands and mount a new orthodontic appliance. For example, as discussed above, unlike the conventional orthodontic devices that include molar bands welded thereto, the expansion device 60 is not welded to the molar bands 63 and 65. As such, the dentist does not need to dismount the existing molar bands 63 and 65 from the molar teeth and, as a consequence, the dentist can easily mount/dismount various types of orthodontic appliances. Also, the dentist can have flexibility in scheduling treatment procedures. For example, he can quickly reinstall the bite plate 13 in the middle of the expansion treatment process.

In FIGS. 1-5, the expansion device 60 is described as an exemplary device that can be detachably mounted to the molar bands. However, it should be apparent to those of ordinary skill that any other suitable appliance having similar adaptors can be mounted to the molar bands without removing the molar bands from the molar teeth of the patient. Also, any other suitable appliance having two wire segments that can be inserted into the tube sections 28 of the adaptors 26 and 27 can be detachably mounted to the molar bands 22 and 23.

Those skilled in the art will appreciate that the methods and designs described above have additional applications and that the relevant applications are not limited to those specifically recited above. Also, the present invention may be embodied in other specific forms without departing from the essential characteristics as described herein. The embodiments described above are to be considered in all respects as illustrative only and not restrictive in any manner.

What is claimed is:

1. A device for applying an orthodontic force, comprising:
   an adaptor including a first section forming a housing and configured to fit directly onto a sheath of a molar band and a second section having an elongated bore formed of a tube extending from the housing; and
   a pin including a first portion having a generally U-shape and a second portion being straight, the second portion being configured to be slidably mounted into the second section of the adaptor,
   wherein the first portion of the pin is adapted to slide into the sheath to thereby detachably lock the adaptor to the molar band and an entire portion of the first portion of the pin is disposed within the housing when the adaptor is detachably locked to the molar band,
   wherein the pin further includes a handle extending vertically from the first portion.

2. A device as recited in claim 1, wherein the adaptor further includes a bump disposed on an outer surface thereof.

3. A device as recited in claim 1, wherein the second portion of the pin is a circular wire.

4. A device as recited in claim 1, wherein the first portion of the pin is formed of a wire.

5. A device as recited in claim 1, wherein the device is an expander.

6. A device as recited in claim 5, further comprising:
   a screw member for adjusting a level of the orthodontic force.

* * * * *